(12) United States Patent
Bollish (10) Patent No.: US 9,931,463 B2
(45) Date of Patent: Apr. 3, 2018

(54) INFUSION CHANNEL IDENTIFIERS

(71) Applicant: CareFusion 303, Inc., San Diego, CA (US)

(72) Inventor: Stephen Bollish, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 147 days.

(21) Appl. No.: 13/830,995

(22) Filed: Mar. 14, 2013

(65) Prior Publication Data
US 2014/0276565 A1    Sep. 18, 2014

(51) Int. Cl.
*A61M 5/145*    (2006.01)
*G06F 19/00*    (2018.01)
*A61M 5/168*    (2006.01)

(52) U.S. Cl.
CPC ....... *A61M 5/1452* (2013.01); *G06F 19/3468* (2013.01); *A61M 5/1684* (2013.01); *A61M 2205/3553* (2013.01); *A61M 2205/3561* (2013.01); *A61M 2205/3584* (2013.01); *A61M 2205/3592* (2013.01); *A61M 2205/502* (2013.01); *A61M 2205/60* (2013.01); *A61M 2205/6009* (2013.01)

(58) Field of Classification Search
CPC .... A61M 2005/14208; A61M 2205/50; A61M 2205/502; A61M 5/142; A61M 5/16827; A61M 2205/3576; A61M 2205/3334; A61M 2205/60; A61M 2205/505; A61M 5/1407; A61M 2205/3553; A61M 2205/3561; A61M 2205/3584; A61M 2205/3592; A61M 2205/6009; A61M 5/1452; A61M 5/168; A61M 5/172; A61M 5/1723; A61M 5/1684; G06F 19/3468

USPC ............ 604/114, 123, 151, 67, 506, 507, 82
See application file for complete search history.

(56) References Cited

U.S. PATENT DOCUMENTS

| | | | | |
|---|---|---|---|---|
| 5,378,231 | A * | 1/1995 | Johnson et al. | 604/67 |
| 5,445,621 | A * | 8/1995 | Poli | A61M 5/1413 604/246 |
| 5,713,856 | A * | 2/1998 | Eggers | A61M 5/1413 604/65 |
| 7,476,204 | B2 * | 1/2009 | Parks et al. | 600/593 |
| 2005/0277912 | A1 * | 12/2005 | John | 604/890.1 |

(Continued)

*Primary Examiner* — Aarti B Berdichevsky
*Assistant Examiner* — Brandy S Lee
(74) *Attorney, Agent, or Firm* — Mintz Levin Cohn Ferris Glovsky and Popeo, P.C.

(57) ABSTRACT

Infusion channel identifiers are generated and used that identify infusion channels transporting medication from an infusion pump to a patient. The infusion pump includes a user interface device, a controller, and at least one infusion device. At a first user interface of the user interface device, data associated with an infusion channel is received. Based on the data, the controller generates an infusion channel identifier identifying the infusion channel. On the first user interface, the infusion channel identifier is displayed. At a second user interface of the user interface device, the infusion channel identifier, a beginning time of a desired provision of the medication to the patient, and a time duration of the desired provision is received. The controller actuates the infusion device and the infusion channel at the beginning time for the time duration. The infusion device delivers, via the infusion channel, the medication to the patient.

9 Claims, 10 Drawing Sheets

(56) References Cited

U.S. PATENT DOCUMENTS

| | | | |
|---|---|---|---|
| 2006/0100746 A1* | 5/2006 | Leibner-Druska | A61M 5/14 700/282 |
| 2006/0241977 A1* | 10/2006 | Fitzgerald | G06F 19/322 705/3 |
| 2007/0255348 A1* | 11/2007 | Holtzclaw | A61B 5/0002 607/60 |
| 2010/0262116 A1* | 10/2010 | Sowb | 604/500 |

* cited by examiner

INFUSION CHANNEL IDENTIFIERS

TECHNICAL FIELD

The current subject matter relates to generation of identifiers for infusion channels delivering medications from at least one infusion device of an infusion pump to at least one anatomical location on a body of a patient.

BACKGROUND

An infusion pump typically provides infusion to a patient via multiple infusion channels. When a number/count of the infusion channels becomes high (for example, more than five), it becomes important to keep an account of a mapping between infusion channels and corresponding medications being transported within those infusion channels. To keep an account of this mapping, a clinician conventionally makes notes on pieces of an adhesive tape, and attaches a corresponding piece of the adhesive tape at each of both ends of every infusion channel. Each note typically indicates a medication flowing through a point where the adhesive tape is stuck, and a location of the end of the adhesive tape other than the end where the adhesive tape is attached. This process of noting medications and mapping medications with infusion channels requires a significant amount of manual effort by the clinician, and consumes a lot of time of the clinician. Further, when the infusion channels need to be changed for sterility concerns or other reasons, the process of noting medications and mapping medications with infusion channels becomes even more tedious. Moreover, when the notes on the adhesive tapes are written in an unclear handwriting by a clinician, the inference of such notes at a later time or by a different clinician are susceptible to error.

SUMMARY

The current subject matter describes generation and use of infusion channel identifiers that identify infusion channels transporting medication from an infusion pump to a patient. The infusion pump can include a user interface device, a controller, and at least one infusion device. At a first user interface of the user interface device, data associated with an infusion channel can be received from a clinician. Based on the data, the controller can generate an infusion channel identifier identifying the infusion channel. On the first user interface, the infusion channel identifier can be displayed. At a second user interface of the user interface device, the infusion channel identifier, a beginning time of a desired provision of the medication to the patient, and a time duration of the desired provision can be received from the clinician. The controller can actuate the infusion device and the infusion channel at the beginning time for the time duration. The infusion device can deliver, via the infusion channel, the medication to the patient. A third user interface of the user interface device can allow the clinician or any other authorized user to search for historical data associated with any infusion channel, the historical data including the beginning time and the time duration. Related apparatus, systems, methods, techniques and articles are also described.

In one aspect, data associated with an infusion channel can be received at a first user interface of a user interface device. The infusion channel can transport medication from an infusion device to a patient. A controller connected to the user interface device can generate, based on the data, an infusion channel identifier identifying the infusion channel. The infusion channel identifier can be displayed on the first user interface.

The data associated with the infusion channel can be received from a clinician. This data can include one or more of: a patient identifier identifying the patient, a location of the infusion device, an infusion device identifier identifying the infusion device, an anatomical location on a body of the patient where the medication is to be infused via the infusion channel, a name of the medication to be infused via the infusion channel, and a concentration of the medication to be infused via the infusion channel.

The infusion channel identifier can uniquely identify the infusion channel. The first user interface can display a graphical display area showing the infusion device, the infusion channel, and a location of infusion on a body of the patient. A click on the displayed infusion channel can display the infusion channel identifier uniquely identifying the infusion channel. The location of infusion can be a vascular access site on the body of the patient.

At a second user interface of the user interface device, the infusion channel identifier, a beginning time of a desired provision of the medication to the patient, and a time duration of the desired provision can be received from a clinician. The controller can actuate the infusion device and the infusion channel at the beginning time for the time duration. The infusion device can deliver the medication to the patient via the infusion channel.

The second user interface can display a graphical display area showing the infusion device, the infusion channel, and a location of infusion on a body of the patient. A click on the displayed infusion channel can display: the infusion channel identifier uniquely identifying the infusion channel, the beginning time, the time duration, and a status of the delivery. The status of delivery can include one of: not yet delivering the medication, about to deliver the medication within a threshold value of time, and delivering the medication.

The infusion channel identifier, the beginning time of the provision of the medication to the patient, and the time duration of the desired provision can be stored in a database connected to the controller. The database can be wirelessly connected to the controller via a communication network.

At a third user interface of the user interface device, a search query comprising the infusion channel identifier can be received from a clinician. The controller can perform a search of the database for historical data associated with the infusion channel identifier. The historical data can include the beginning time and the time duration. The historical data associated with the infusion channel identifier can be displayed on the third user interface.

In another aspect, a system includes a user interface device, a plurality of infusion devices, and a controller. The user interface device can execute a user interface that can receive data associated with a plurality of infusion channels that are used to deliver medication to a plurality of locations on a body of a patient. The plurality of infusion devices can deliver the medication to the plurality of locations on the body of the patient via the plurality of infusion channels. The controller can be connected to the user interface device and the plurality of infusion devices. The controller can generate a plurality of infusion channel identifiers for the plurality of infusion channels based on the received data.

The user interface can receive data from a clinician. The data associated with each infusion channel of the plurality of infusion channels can include: a patient identifier identifying the patient, a physical location of an infusion device connected to the infusion channel, an infusion device identifier identifying the infusion device, an anatomical location on a body of the patient where the medication is to be infused, a name of the medication to be infused, and a concentration of the medication to be infused.

The controller can be wirelessly connected to the user interface device via a communication network. The plurality of infusion devices can be a plurality of infusion modules of an infusion pump. The user interface device, the controller, and the plurality of infusion devices can be portions of an infusion pump packaged as a single device. Each infusion channel identifier can uniquely identify a corresponding infusion channel. The user interface can display a graphical display area showing the plurality of infusion devices, the plurality of infusion channels, and the locations on the body of the patient. A click on a displayed infusion channel displays an infusion channel identifier that uniquely identifies the infusion channel. The location is a point on a vein of an arm of the body of the patient.

In yet another aspect, at a user interface of a user interface device, an infusion channel identifier, a beginning time of desired infusion of medication, and a time duration of the desired infusion can be received. The infusion channel identifier can identify an infusion channel used to deliver the medication from an infusion device to a patient. A controller can be connected to the user interface device. The controller can actuate the infusion device and the infusion channel at the beginning time for the time duration. The infusion device can deliver the medication to the patient via the infusion channel.

The infusion channel identifier, the beginning time, and the time duration can be received from a clinician. The user interface can display a graphical display area showing the infusion device, the infusion channel, and a location of infusion on a body of the patient. A click on the displayed infusion channel can display the infusion channel identifier, the beginning time, the time duration, and a status of the delivery. The status of delivery can include one of: not yet delivering the medication, about to deliver the medication within a threshold value of time, and currently delivering the medication.

Computer program products are also described that comprise non-transitory computer readable media storing instructions, which when executed by one data or more processors of one or more computing systems, causes at least one data processor to perform operations herein. Similarly, computer systems are also described that may include one or more data processors and a memory coupled to the one or more data processors. The memory may temporarily or permanently store instructions that cause at least one processor to perform one or more of the operations described herein. In addition, methods can be implemented by one or more data processors either within a single computing system or distributed among two or more computing systems.

The subject matter described herein provides many advantages. For example, the current subject matter described generation of infusion channel identifiers, thereby preventing the clinician to perform a labor-intensive hand-written labeling of each infusion channel. Further, the computationally generated infusion channel identifiers are easy to read, as opposed to the hand-written labels, reading of which can be highly susceptible to error.

Furthermore, the generated infusion channel identifiers can be used to actuate a provision of a medication via the infusion channel identified by the infusion channel identifier. Such a computational actuation can save the time of a clinician.

Moreover, the generated infusion channel identifiers can be stored along with flow data (for example, beginning time of provision of medication, time duration of the provision of medication) associated with each infusion channel, as specified by a clinician. Such storage allows a clinician to later search the historical flow data associated with each infusion channel. The historical flow data can be used to determine a remaining lifetime of the infusion channel, and can be used to perform statistical analyses that can be useful for hospitals and infusion channel manufacturers. Additionally, the historical flow data can be used to identify: a patient to whom the medication is infused, a location of the infusion, an infusion device providing the infusion to the infusion channel, an anatomical location of the infusion on a body of the patient, a name of a medication that was infused, and a concentration of the medication that was infused.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

Like reference symbols in the various drawings indicate like elements.

DETAILED DESCRIPTION

Figure 1:
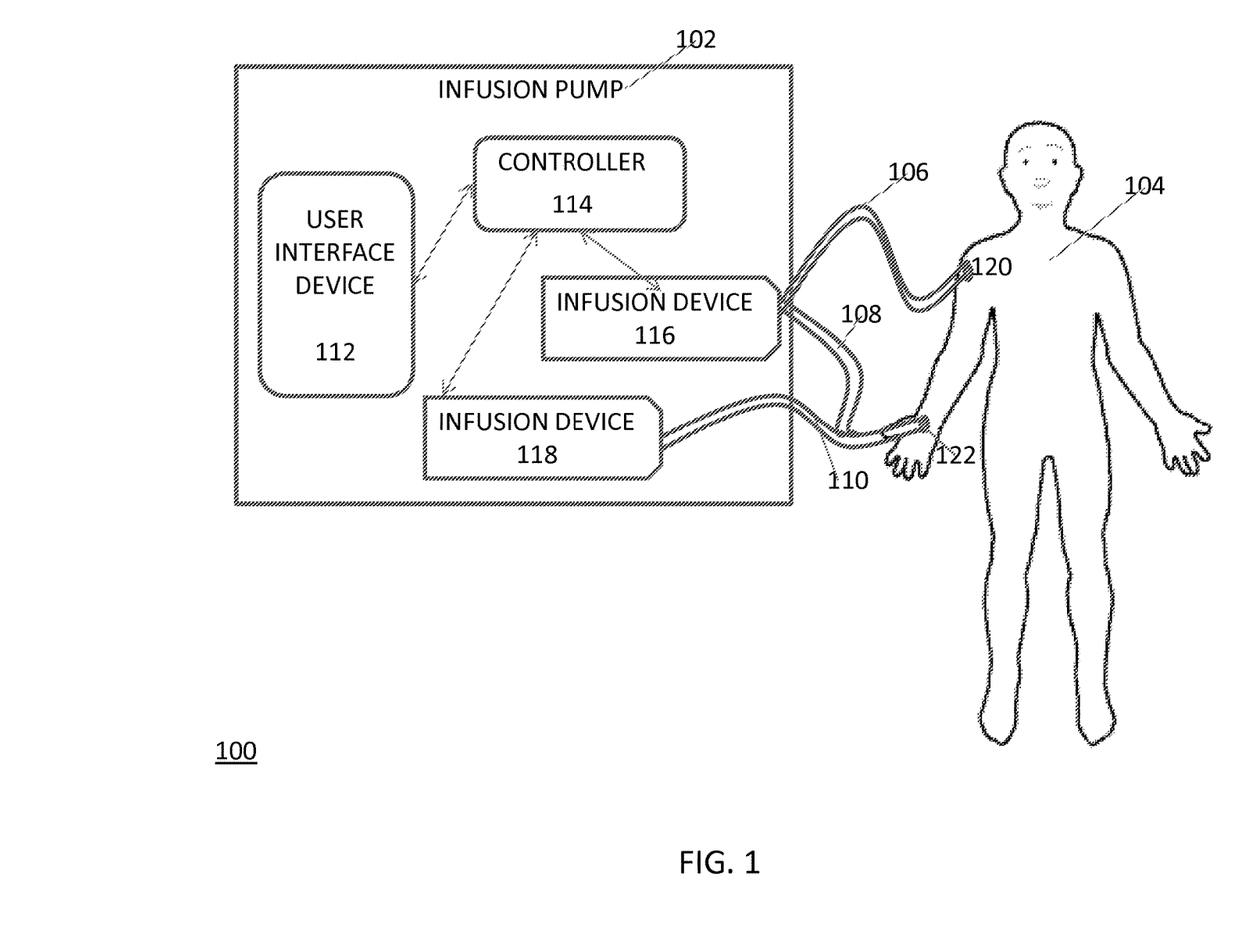
FIG. 1 is a diagram illustrating an infusion pump that provides one or more medications to a patient via infusion channels.

FIG. 1 is a diagram 100 illustrating an infusion pump 102 that provides one or more medications to a patient 104 via infusion channels 106, 108, and 110. The infusion pump 102 includes a user interface device 112, a controller 114, and infusion devices 116 and 118. The infusion channel 106 transports medication from the infusion device 116 to a first location 120 on a body of the patient 104. The infusion channel 108 transports medication from the infusion device 116 to a second location 122 on a body of the patient 104. The infusion channel transports medication from the infusion device 118 to the second location 122 on a body of the patient 104. Some portion of the infusion channel 108 can overlap with some portion of the infusion channel 110 so as to mix medications from respective infusion devices 116 and 118.

A clinician can input data associated with an infusion channel on a first user interface displayed by the user interface device 112. Based on the input data, the controller 114 can generate an infusion channel identifier for the infusion channel. The user device 112 can the display the infusion channel identifier on the first user interface.

If an infusion channel identifier identifying an infusion channel has already been generated, the clinician can input data specifying the infusion channel identifier and a time duration for which medication should be delivered via the infusion channel on a second user interface displayed by the user interface device 112. Based on this input data, the controller 114 can activate the associated infusion device and the corresponding infusion channel for the specified time duration. The associated infusion device can deliver the medication via the activated infusion channel for as long as the infusion device remains activated.

The infusion pump 102 can be connected to an external device, such as a printer. The printer can print, either automatically or based on individual commands of the clinician, the generated infusion channel identifier. The clinician can optionally attach the printed infusion channel identifier to the infusion channel.

The clinician can be a doctor or a nurse. In some variations, the clinician can be a pharmacist, an assistant or associate in a hospital or laboratory, a psychologist, a psychiatrist, and/or any other authorized individual. In some implementations, the clinician can be the patient 104.

The user interface device 112 can be a computer or a tablet computer. The user interface device 112 can receive input from the clinician and can display an output to the clinician. To receive input, the user interface device 112 can be a touch screen device or can be attached with an input device, such as a mouse, a joystick, a keyboard, a voice detection device, or any other input device. To provide output, the user device 112 can include a display screen, which can be a cathode ray tube (CRT) monitor, a liquid crystal display (LCD) monitor, a light emitting diode (LED) monitor, or any other display screen.

The controller 114 can be one or more of: one or more microcontrollers, one or more microprocessors, one or more computers, one or more servers, and the like.

The infusion devices 116 and 118 can be mechanical devices that can deliver medications to a body of the patient 104 via the infusion channels 106, 108, and 110. The controller 114 can control the activations and movements of the infusion devices 116 and 118. The infusion devices can be infusion modules of the infusion pump. In some implementations, the infusion device 16 and/or 118 can include a plunger and syringe. The controller 114 can turn a screw that can push on the plunger in accordance with the infusion channel identifiers and time durations specified by the clinician. In some implementations, the controller 114 can be embedded with at least one of the infusion devices 116 and 118.

The infusion channels 106, 108, and 110 can have circular or oval cross-sections. Although circular and oval cross-sections are described, the infusion channels can have other shapes of cross-sections, such as a square, a rectangle, a triangle, a hexagon, a polygon, or any other shape. The infusion channels can be made of rubber, silicone, or any other material.

The clinician can deactivate one or more infusion channels 106, 108, and 110 by removing at least a portion of the tubing forming the infusion channel. In other implementations, to deactivate an infusion channel 106, 108, or 110, the clinician can occlude the infusion channel by placing a clamp or stopcock in the infusion channel such that the desired infusion channel is occluded while not affecting other infusion channels. The clamp can be one or more of: a roller clamp, a slide clamp, a stopcock and any other such device. To activate or re-activate an infusion channel 106, 108, or 110, the clinician can remove the clamp from the infusion channel.

Although three infusion channels 106, 108, and 110 have been described, in some implementations, one or more than two infusion channels can be used. Although two infusion devices 116 and 118 have been described, in other implementations, one or more than two infusion devices can be used. Although two locations 120 and 122 on a body of the patient 104 have been described, in alternate implementations, one or more than two locations can be present.

Figure 2:
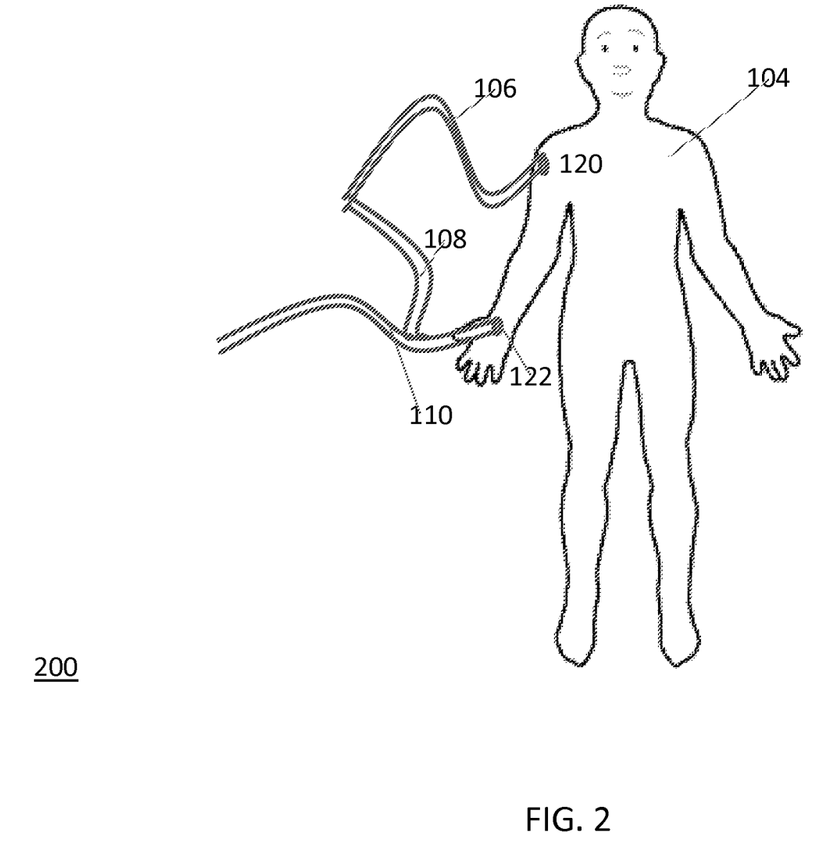
FIG. 2 is a diagram illustrating a patient receiving one or more medications via infusion channels at locations on a body of the patient.

FIG. 2 is a diagram 200 illustrating a patient 104 receiving one or more medications via infusion channels 106, 108, and 110 at locations 120 and 122 on a body of the patient 104. The infusion locations 120 and 122 on the body of the patient can be veins on the arm of the patient 104. Although locations 120 and 122 are shown on the arm of the patient 104, other locations are also possible, such as hands, chest, neck, scalp or any other location where veins can be located.

Figure 3:
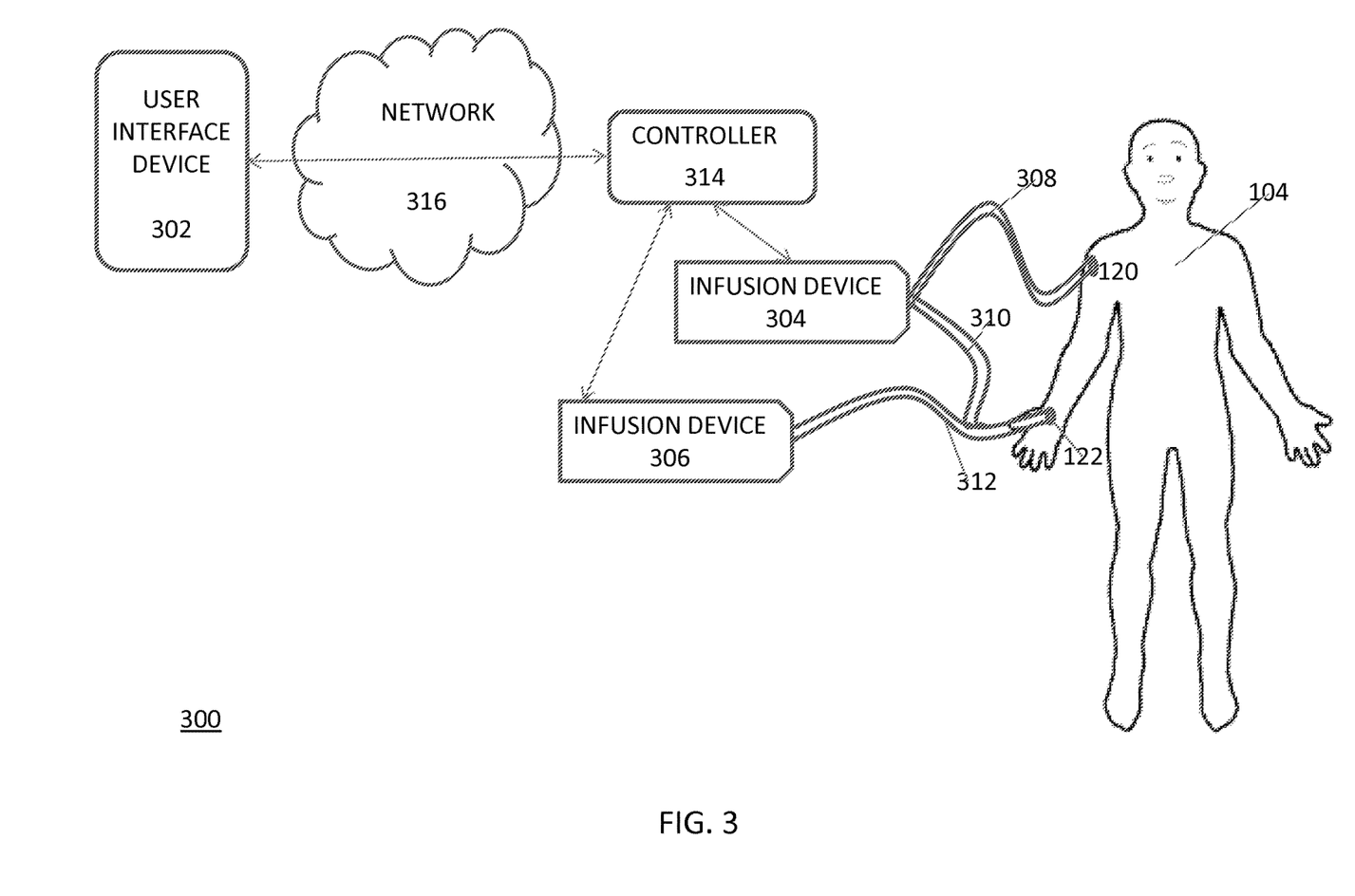
FIG. 3 is a diagram illustrating a user interface device being wirelessly connected with infusion devices that can provide medication to a patient.

FIG. 3 is a diagram 300 illustrating a user interface device 302 being wirelessly connected with infusion devices 304 and 306 that can provide medication to a patient 104. The clinician can specify the infusion channel identifier and time duration of provision of medication on the user interface device 302. The infusion devices 304 and 306 can provide medication to the patient 104 via infusion channels 308, 310 and 312. The controller 314 can actuate the infusion devices 304 and 306 in accordance with infusion channel identifiers and corresponding time durations of provision of medication specified by the clinician on the user interface device 302. The user interface 302 can be connected to the controller via a communication network 316. The communication network 316 can be one or more of: a local area network, a metropolitan area network, a wide area network, a BLUETOOTH network, an infrared network, internet, or any other network.

In some implementations, the user interface device 302 can be same as the user interface device 112. The controller 314 can be same as the controller 114. The infusion devices 304 and 306 can be same as the infusion devices 116 and 118, respectively. The infusion channels 308, 310 and 312 can be same as infusion channels 106, 108, and 110.

Figure 4:
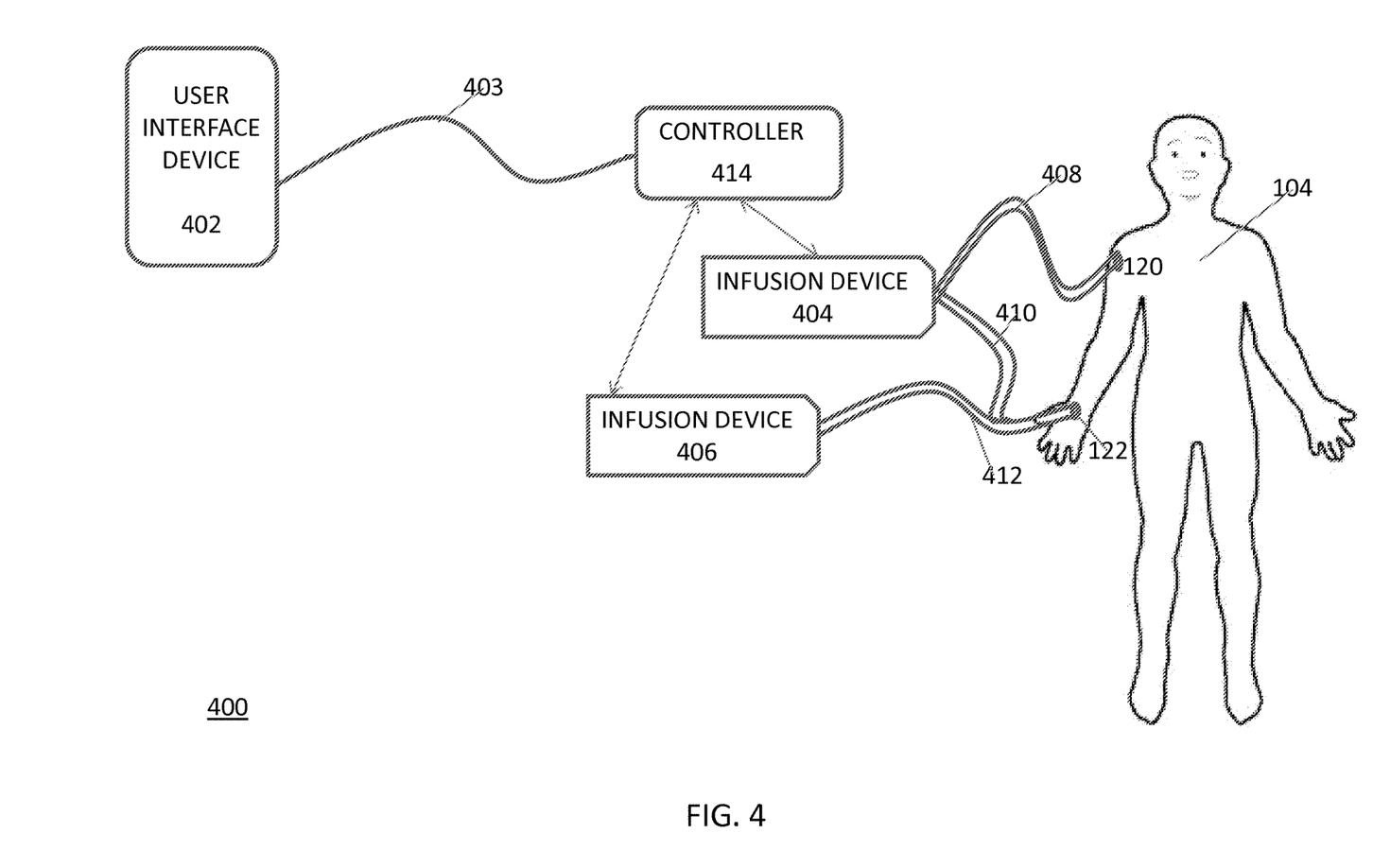
FIG. 4 is diagram illustrating a user interface device being connected, via one or more wires, with infusion devices that can provide medication to a patient.

FIG. 4 is diagram 400 illustrating a user interface device 402 being connected, via one or more wires 403, with infusion devices 404 and 406 that can provide medication to a patient 104. The clinician can specify the infusion channel identifier and time duration of provision of medication on the user interface device 402. The infusion devices 404 and 406 can provide medication to the patient 104 via infusion channels 408, 410 and 412. The controller 414 can actuate the infusion devices 404 and 406 in accordance with infusion channel identifiers and corresponding time durations of provision of medication specified by the clinician on the user interface device 402. The user interface 402 can be connected to the controller via a network 416. The network 416 can be one or more of: a local area network, a metropolitan area network, a wide area network, a BLUETOOTH network, an infrared network, internet, or any other network.

In some implementations, the user interface device 402 can be same as the user interface device 112. The controller 414 can be same as the controller 114. The infusion devices 404 and 406 can be same as the infusion devices 116 and 118, respectively. The infusion channels 408, 410 and 412 can be same as infusion channels 106, 108, and 110.

Figure 5:
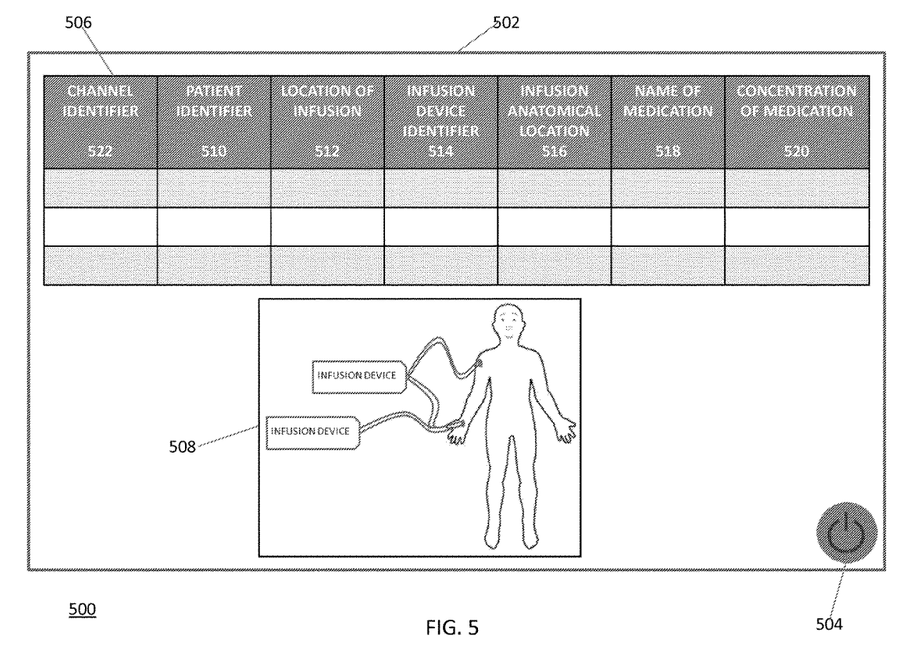
FIG. 5 is a diagram illustrating a user interface used to generate infusion channel identifiers that identify corresponding infusion channels.

FIG. 5 is a diagram 500 illustrating a user interface 502 used to generate infusion channel identifiers that identify corresponding infusion channels. The user interface 502 can be executed on the user interface device 112, 302, or 402.

The user interface 502 can display a power button 504, which can be selected by a clinician to power on or off at least one of the user interface 502 and the user interface device 112, 302, or 402. This powering off may not stop a scheduled delivery of the medication via the infusion channels. However, the user interface 502 can include other buttons that can be used to stop, pause, restart, and/or cancel a scheduled delivery of the medication via any infusion channel.

The user interface 502 can include an infusion channel identifier generation area 506 and a graphical display area 508.

The infusion channel identifier generation area 506 can display a selection of values for each of the following parameters associated with an infusion channel: a patient identifier 510, a location 512 of infusion, an infusion device identifier 514, an anatomical location 516 of infusion, a name 518 of a medication to be infused, and a concentration 520 of the medication to be infused. In some implementations, the displayed values of each of these parameters can be specific for every hospital. In one variation, the clinician can specify a custom/new value for one or more of these parameters, rather than selecting a value from predetermined values for each parameter.

The patient identifier 510 can be one or a combination of: name of the patient 104, date of birth of the patient 104, social security of the patient 104, a unique number allocated to the patient 104 by the hospital, and other data of the patient 104. The patient identifier 510 can be unique for each patient 104. The location 512 of the infusion can be a precise physical location where the infusion is administered, such as a particular clinician's (for example, Dr. Smith's) office. The location 512 can include a detailed address (for example, address, ward number, and bed number) when the infusion is administered in a large hospital. The infusion device identifier 514 can be same as a unique number that can be provided by a manufacturer of the infusion device. The infusion anatomical location 516 can be one of: a top location on the arm, a bottom location on the forearm, a middle location behind the elbow, and/or any other location. The name 518 of medication can be either the generic name or the chemical name of the medication that is to be infused.

The user interface device 112, 302, or 402 that implements the user interface 502 sends the input values of the parameters 510, 512, 514, 516, 518, and 520 to the controller 114, 314, or 414. The controller 114, 314, or 414 then generates an infusion channel identifier for each channel, values of parameters of which are input by the clinician. The infusion channel identifier can be unique for each channel. In some implementations, the controller 114, 314, or 414 can generate a unique infusion channel identifier by using standard classes in various programming languages, such as the universally unique identifier (UUID) class in Java. The controller sends the generated unique infusion channel identifiers to the user interface device 112, 302, or 402, which then displays the generated unique infusion channel identifiers 522 in the infusion channel identifier generation area 506.

The graphical display area 508 can display the infusion channels that provide the medication from the infusion devices to the locations on the patient. The clinician can click on any displayed infusion channel, and if an infusion channel identifier for the displayed infusion channel has already been generated, the user interface 502 also displays the generated infusion channel identifier next to the displayed infusion channel.

Figure 6:
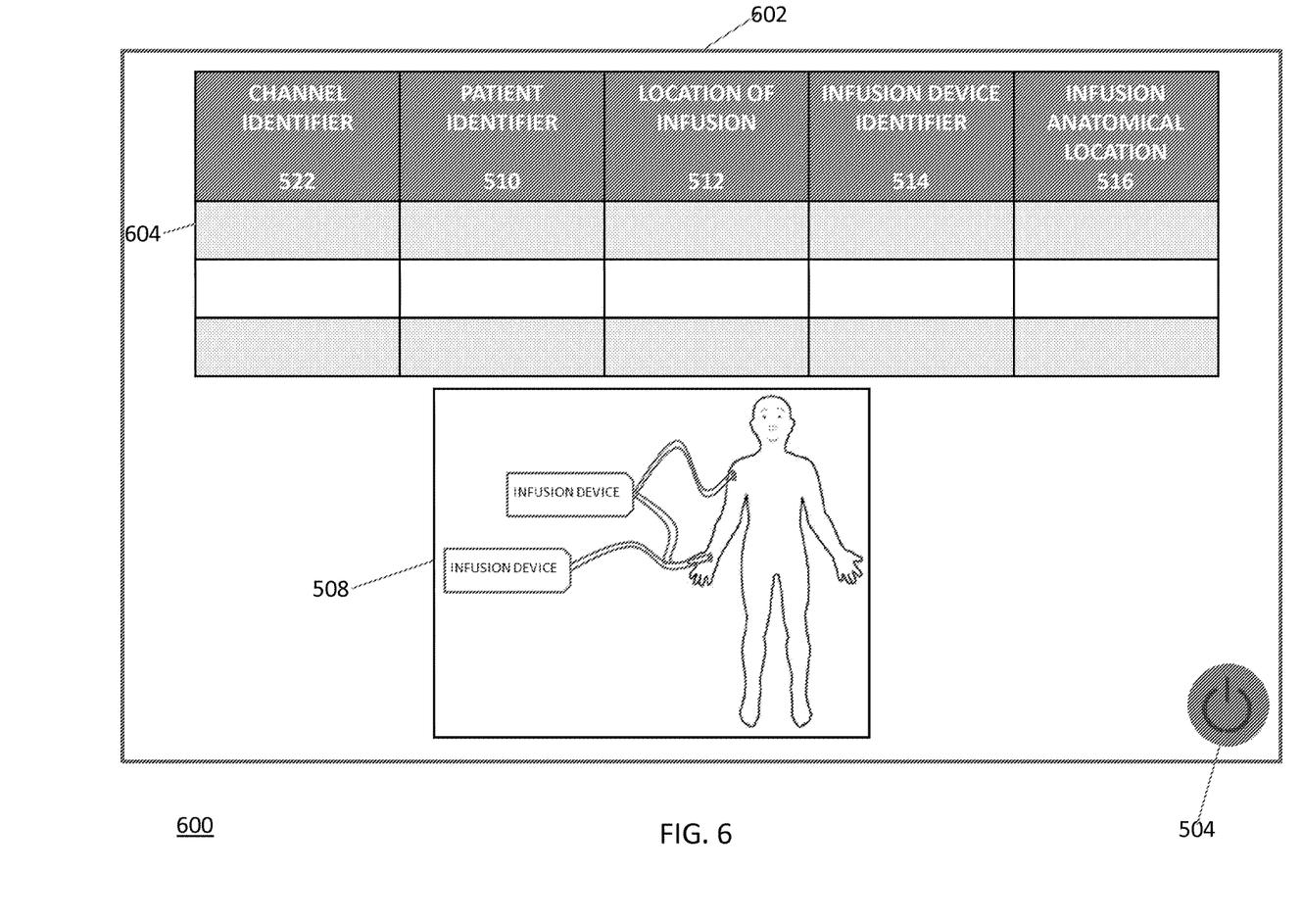
FIG. 6 is another diagram illustrating a user interface used to generate infusion channel identifiers that identify corresponding infusion channels.

FIG. 6 is a diagram 600 illustrating a user interface 602 used to generate infusion channel identifiers that identify corresponding infusion channels. The user interface 602 can be a variation of the user interface 502 when the medication is predetermined and remains the same for every infusion.

The user interface can include an infusion channel identifier generation area 604 and a graphical display area 508. The infusion channel identifier generation area 604 can display a selection of values for each of the following parameters associated with an infusion channel: a patient identifier 510, a location 512 of infusion, an infusion device identifier 514, and an anatomical location 516 of infusion. In one variation, the clinician can specify a custom/new value for one or more of these parameters, rather than selecting a value from predetermined values for each parameter. The infusion channel identifier 522 for each channel can be generated based on the selected and/or specified values of these parameters, and then displayed in the infusion channel identifier generation area 604.

While the user interface 602 is described as a variation of the user interface 502, there can be other variations of the user interface 502 where one or more of the parameters 510, 512, 514, 516, 518, and 520 may not be present. For example, when there is a single infusion device, the corresponding user interface to generate unique infusion channel identifiers may not include the infusion device identifier 514.

Figure 7:
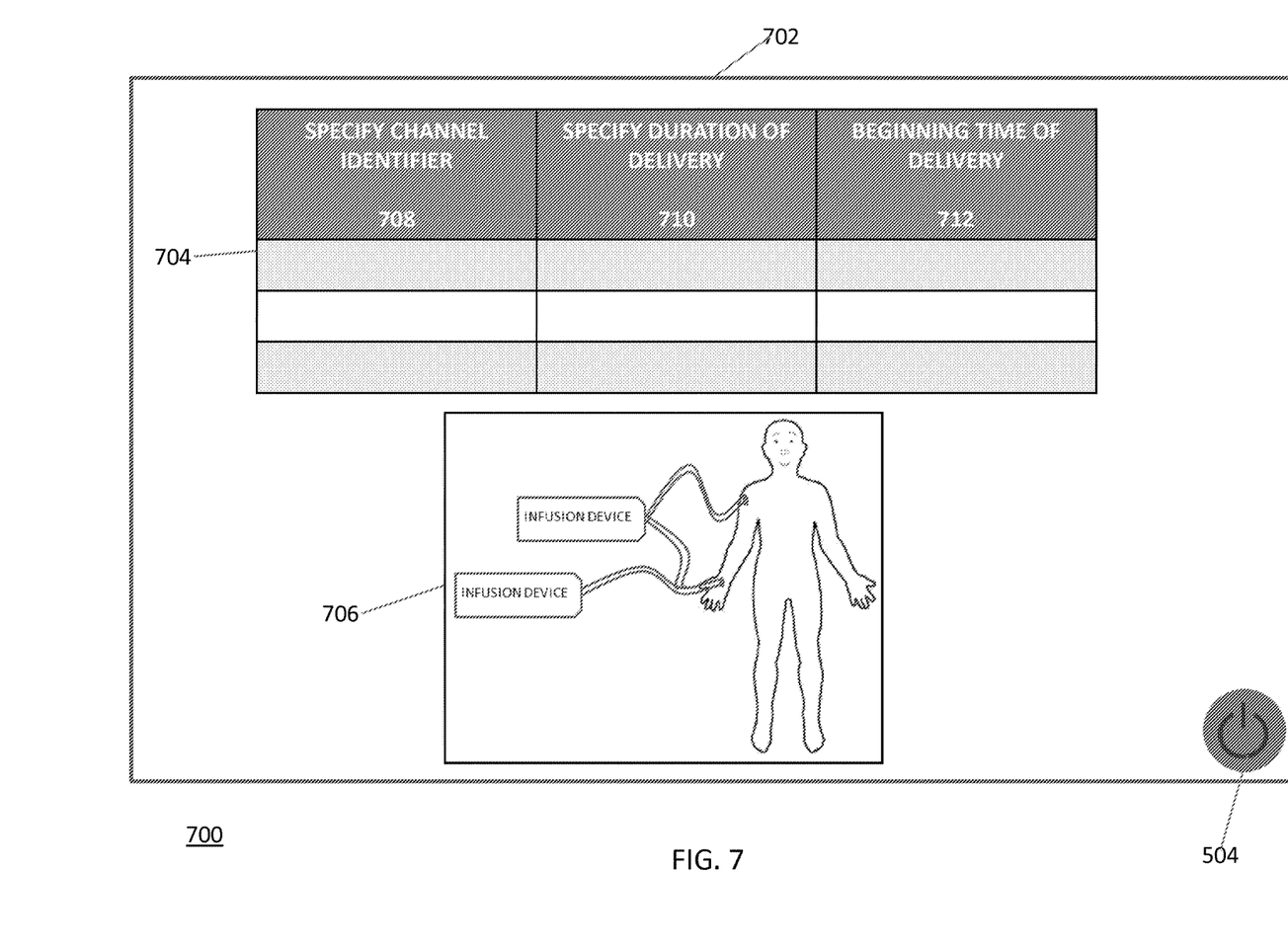
FIG. 7 is a diagram illustrating a user interface used to specify an infusion channel identifier and corresponding time duration of delivery.

FIG. 7 is a diagram 700 illustrating a user interface 702 used to specify an infusion channel identifier and corresponding time duration of delivery. The user interface 702 can be executed on the user interface device 112, 302, or 402. The user interface 702 can include a planning area 704 and a graphical display area 706.

The planning area 704 allows a clinician to provide a value of an infusion channel identifier 708, a time duration 710 of delivery of medication via an infusion channel identified by the infusion channel identifier, and a beginning time 712 of the delivery of the medication.

The graphical display area 706 can display the infusion channels that provide the medication from the infusion devices to the locations on the patient. The clinician can click on any displayed infusion channel, and if the infusion channel identifier, time duration of delivery and the beginning time for the delivery via the displayed infusion channel has already been specified, the graphical area 706 also displays the generated infusion channel identifier, the time duration of delivery, and beginning time next to the displayed infusion channel. Additionally, when a user clicks on a displayed infusion channel, the color of the infusion channel can be red if the infusion is in an alarm state (for example, if the infusion is unreasonably high, if the infusion has not begun at an expected point in time, or any other alarming state), yellow if the infusion is about to start in about a threshold time (for example, 10 seconds, 30 seconds, 2 minutes, 5 minutes, 10 minutes, or any other value), and green if the infusion is already taking place.

A database connected to the controller (114, 314, 414) can store data entered in the planning area 702 by the clinician. In one implementation, this database can be a part of the infusion pump 102. In another implementation, this database can be located at a remote server that is wirelessly connected with the controller (114, 314, 414) via a communication network. A third user interface on the user interface device (112, 302, 402) can allow the clinician or any other authorized individual (which can be the patient 104 in some implementations) to search for data in this database so as to search for historical delivery schedules associated with particular one or more infusion channels.

Figure 8:
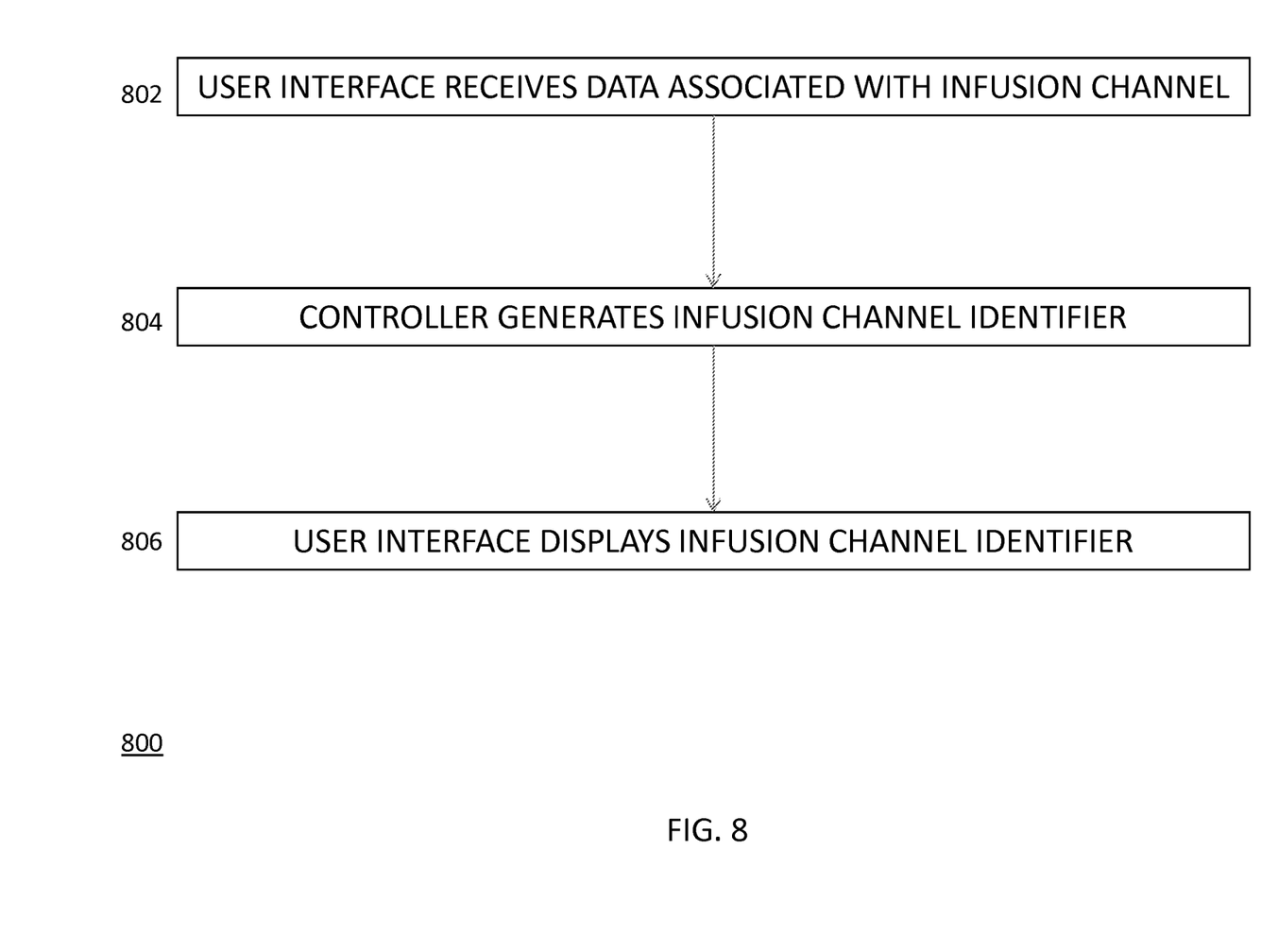
FIG. 8 is a flow diagram illustrating a generation and display of an infusion channel generator.

FIG. 8 is a process flow diagram 800 illustrating generation and display of an infusion channel generator. A user interface 502 implemented on a user interface device (112, 302, 402) can receive, at 802 and from a clinician, data associated with an infusion channel. This data can include values of parameters including: a patient identifier 510, a location 512 of infusion, an infusion device identifier 514, an anatomical location 516 of infusion, a name 518 of a medication to be infused, and a concentration 520 of the medication to be infused. The user interface device (112, 302, 402) can send the values of the parameters to a controller (114, 314, 414). The controller (114, 314, 414) can generate, at 804, an infusion channel identifier that can uniquely identify the infusion channel. The controller (114, 314, 414) can send the generated infusion channel identifier to the user interface device (112, 302, 402). The user interface 502 can then display, at 806, the infusion channel identifier in column 522.

Figure 9:
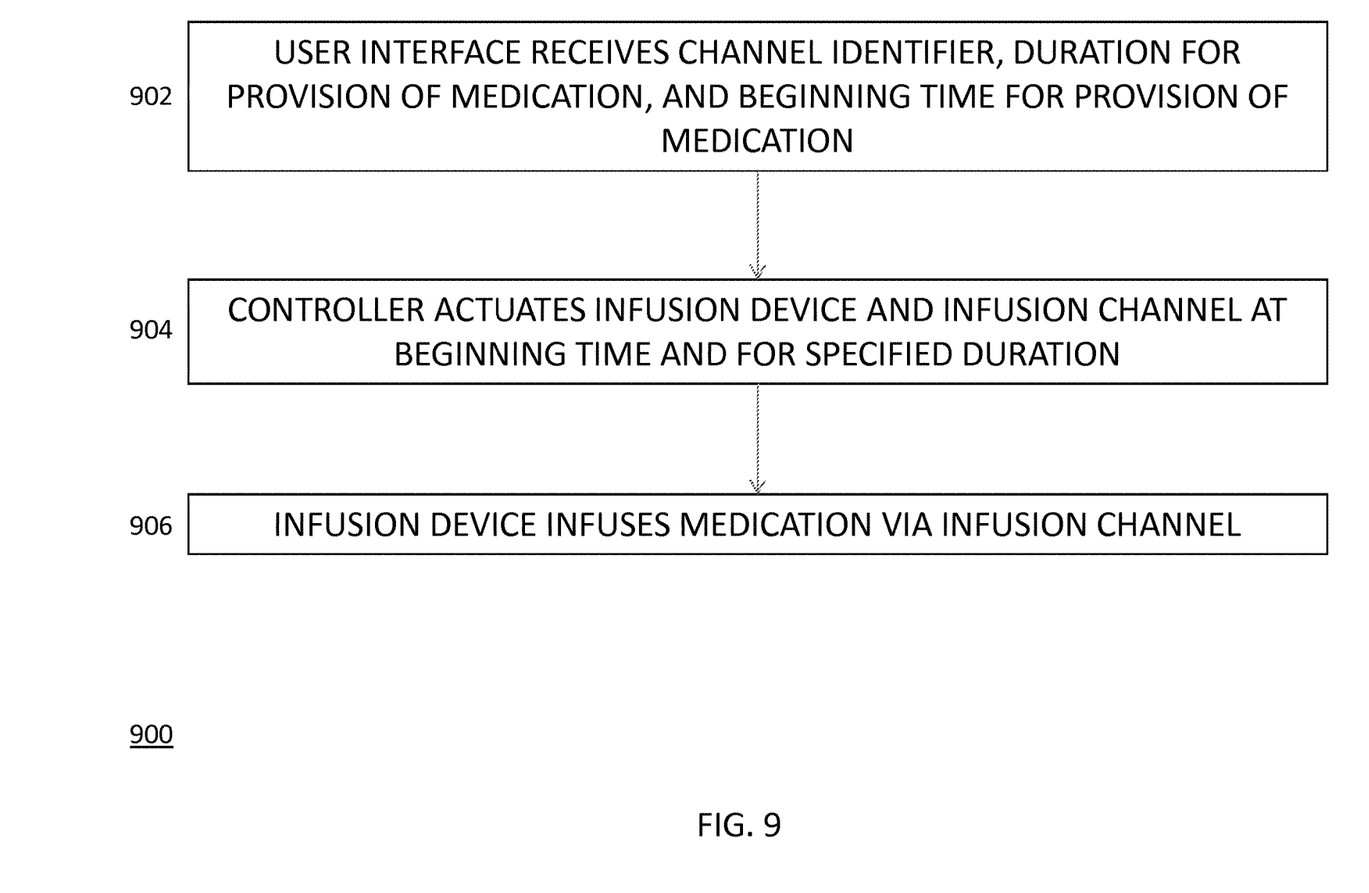
FIG. 9 is a flow diagram illustrating a use of generated infusion channel identifiers for providing a medication at times specified by a clinician.

FIG. 9 is a process flow diagram 900 illustrating a use of generated infusion channel identifiers for providing a medication at times specified by a clinician. The user interface 702 implemented on a user interface device (112, 302, 402) can receive, at 902 and from a clinician, an infusion channel identifier, a time duration for provision of medication, and a beginning time for provision of the medication. The user interface device (112, 302, 402) can then send, at 904, the values of the infusion channel identifier, the time duration, and the beginning time to a controller (114, 314, 414). The controller (114, 314, 414) can actuate, at 904, the infusion device (116, 118, 304, 306, 404, or 406) and the infusion channel (106, 108, 110, 308, 310, 312, 408, 410, or 412) at the beginning time and for the specified time duration. The actuated infusion device (116, 118, 304, 306, 404, or 406) can then infuse the medication via the actuated infusion channel (106, 108, 110, 308, 310, 312, 408, 410, or 412).

Figure 10:
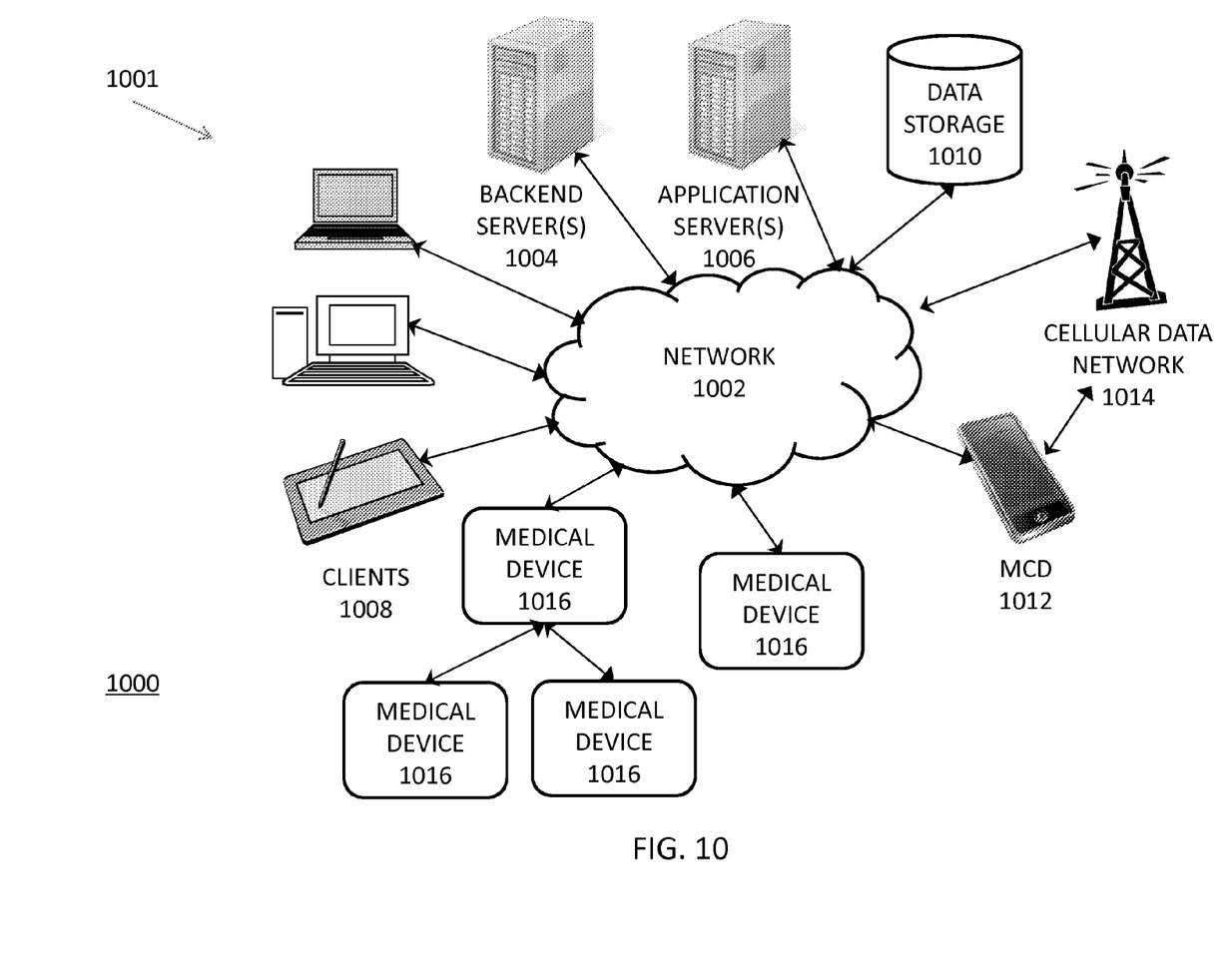
FIG. 10 is a system diagram illustrating a computing landscape that can include the infusion pump, the user interface device, the controller, and the infusion devices within a healthcare environment.

FIG. 10 is a system diagram 1000 illustrating a computing landscape 1001 that can include the infusion pump 102 (which can be one of medical devices 1016), the user interface device (112, 302, 402), the controller (114, 314, 414), and the infusion devices (116, 118, 304, 306, 404, 406) within a healthcare environment, such as a hospital, a clinic, a laboratory, or any other environment. Various devices and systems, both local to the healthcare environment and remote from the healthcare environment, can interact via at least one computing network 1002. This computing network 1002 can provide any form or medium of digital communication connectivity (i.e., wired or wireless) amongst the various devices and systems. Examples of communication networks include a local area network ("LAN"), a wide area network ("WAN"), and the Internet. In some cases, one or more of the various devices and systems can interact directly via peer-to-peer coupling (either via a hardwired connection or via a wireless protocol such as Bluetooth or WiFi). In addition, in some variations, one or more of the devices and systems communicate via a cellular data network.

In particular, aspects of the computing landscape 1001 can be implemented in a computing system that includes a back-end component (e.g., as a data server 1004), or that includes a middleware component (e.g., an application server 1006), or that includes a front-end component (e.g., a client computer 1008 having a graphical user interface or a Web browser through which a user can interact with an implementation of the subject matter described herein), or any combination of such back-end, middleware, or front-end components. A client 1008 and servers 1004 and 1006 are generally remote from each other and typically interact through the communications network 1002. The relationship of the clients 1008 and servers 1004, 1006 arises by virtue of computer programs running on the respective computers and having a client-server relationship to each other. Clients 1008 can be any of a variety of computing platforms that include local applications for providing various functionalities within the healthcare environment. Example clients 1008 include, but are not limited to, desktop computers, laptop computers, tablets, and other computers with touch-screen interfaces. The local applications can be self-contained in that they do not require network connectivity and/or they can interact with one or more of the servers 1004, 1006 (e.g., a web browser).

A variety of applications can be executed on the various devices and systems within the computing landscape such as electronic health record applications, medical device monitoring, operation, and maintenance applications, scheduling applications, billing applications and the like.

The network 1002 can be coupled to one or more data storage systems 1010. The data storage systems 1010 can include databases providing physical data storage within the healthcare environment or within a dedicated facility. In addition, or in the alternative, the data storage systems 1010 can include cloud-based systems providing remote storage of data in, for example, a multi-tenant computing environment. The data storage systems 1010 can also comprise non-transitory computer readable media.

Mobile communications devices 1012 can also form part of the computing landscape 1001. The mobile communication devices 1012 can communicate directly via the network 1002 and/or they can communicate with the network 1002 via an intermediate network such as a cellular data network 1014. Various types of communication protocols can be used by the mobile communication devices 1012 including, for example, messaging protocols such as SMS and MMS.

Various types of medical devices 1016 can be used as part of the computing landscape 1001. The medical devices 1016 can include one or more of the medical device 102, the user interface 106, the controller 108, and the infusion device 110. These medical devices 1016 can include, unless otherwise specified, any type of device or system with a communications interface that characterizes one or more physiological measurements of a patient and/or that characterize treatment of a patient. In some cases, the medical devices 1016 communicate via peer to peer wired or wireless communications with another medical device 1016 (as opposed to communicating with the network 1002). For example, the medical device 1016 can comprise a bedside vital signs monitor that is connected to other medical devices 1016, namely a wireless pulse oximeter and to a wired blood pressure monitor. One or more operational parameters of the medical devices 1016 can be locally controlled by a clinician, controlled via a clinician via the network 1002, and/or they can be controlled by one or more of a server 1004 and/or 1006, a client 1008, a mobile communication device 1012, and/or another medical device 1016.

The computing landscape 1001 can provide various types of functionality as can be required within a healthcare environment such as a hospital. For example, a pharmacy can initiate a prescription via one of the client computers 1008. This prescription can be stored in the data storage 1010 and/or pushed out to other clients 1008, a mobile communication device 1012, and/or one or more of the medical devices 1016. In addition, the medical devices 1016 can provide data characterizing one or more physiological measurements of a patient and/or treatment of a patient (e.g., medical device 1016 can be an infusion management system, etc.). The data generated by the medical devices 1016 can be communicated to other medical devices 1016, the servers 1004 and 1006, the clients 1008, the mobile communication devices 1012, and/or stored in the data storage systems 1010.

Various implementations of the subject matter described herein can be realized/implemented in digital electronic circuitry, integrated circuitry, specially designed application specific integrated circuits (ASICs), computer hardware, firmware, software, and/or combinations thereof. These various implementations can be implemented in one or more computer programs. These computer programs can be executable and/or interpreted on a programmable system. The programmable system can include at least one programmable processor, which can be have a special purpose or a general purpose. The at least one programmable processor can be coupled to a storage system, at least one input device, and at least one output device. The at least one programmable processor can receive data and instructions from, and can transmit data and instructions to, the storage system, the at least one input device, and the at least one output device.

These computer programs (also known as programs, software, software applications or code) can include machine instructions for a programmable processor, and can be implemented in a high-level procedural and/or object-oriented programming language, and/or in assembly/machine language. As can be used herein, the term "machine-readable medium" can refer to any computer program product, apparatus and/or device (for example, magnetic discs, optical disks, memory, programmable logic devices (PLDs)) used to provide machine instructions and/or data to a programmable processor, including a machine-readable medium that can receive machine instructions as a machine-readable signal. The term "machine-readable signal" can refer to any signal used to provide machine instructions and/or data to a programmable processor.

To provide for interaction with a user, the subject matter described herein can be implemented on a computer that can display data to one or more users on a display device, such as a cathode ray tube (CRT) device, a liquid crystal display (LCD) monitor, a light emitting diode (LED) monitor, or any other display device. The computer can receive data from the one or more users via a keyboard, a mouse, a trackball, a joystick, or any other input device. To provide for interaction with the user, other devices can also be provided, such as devices operating based on user feedback, which can include sensory feedback, such as visual feedback, auditory feedback, tactile feedback, and any other feedback. The input from the user can be received in any form, such as acoustic input, speech input, tactile input, or any other input.

The subject matter described herein can be implemented in a computing system that can include at least one of a back-end component, a middleware component, a front-end component, and one or more combinations thereof. The back-end component can be a data server. The middleware component can be an application server. The front-end component can be a client computer having a graphical user interface or a web browser, through which a user can interact with an implementation of the subject matter described herein. The components of the system can be interconnected by any form or medium of digital data communication, such as a communication network. Examples of communication networks can include a local area network, a wide area network, internet, intranet, Bluetooth network, infrared network, or other networks.

The computing system can include clients and servers. A client and server can be generally remote from each other and can interact through a communication network. The relationship of client and server can arise by virtue of computer programs running on the respective computers and having a client-server relationship with each other.

Although a few variations have been described in detail above, other modifications can be possible. For example, the logic flows depicted in the accompanying figures and described herein do not require the particular order shown, or sequential order, to achieve desirable results. Other embodiments may be within the scope of the following claims.

What is claimed is:

1. A system comprising:
    a user interface device to execute a user interface that receives data associated with a plurality of infusion channels that are used to respectively deliver medication to a different one of a plurality of locations on a body of a patient;
    a plurality of infusion devices to deliver the medication to the plurality of locations on the body of the patient via the plurality of infusion channels; and
    a controller connected to the user interface device and the plurality of infusion devices, the controller generating a plurality of computer-generated, unique infusion channel identifiers for display on the user interface device, wherein each unique infusion channel identifier corresponds to a single infusion channel of the plurality of infusion channels based on the received data, the received data containing one or more values inputted via the user interface device and corresponding to one or more parameters associated with each infusion channel in the plurality of infusion channels, the values including at least one of the following: a historical value, a predetermined value, and a new value, wherein the medication is delivered using an infusion channel in the plurality of infusion channels based on the corresponding generated infusion channel identifier; and
    wherein the user interface concurrently displays (i) a planning area providing tabular format data characterizing the data associated with each of the plurality of infusion channels, and (ii) a graphical display area that includes a graphical representation of the body for the patient graphically identifying locations on the body at which each infusion channel delivers medication.

2. The system of claim 1, wherein the data associated with each infusion channel of the plurality of infusion channels comprises:
    a patient identifier identifying the patient,
    a physical location of an infusion device connected to the infusion channel,
    an infusion device identifier identifying the infusion device, an anatomical location on a body of the patient where the medication is to be infused, a name of the medication to be infused, and a concentration of the medication to be infused.

3. The system of claim 1, wherein the controller is wirelessly connected to the user interface device via a communication network.

4. The system of claim 1, wherein the plurality of infusion devices are a plurality of infusion modules of an infusion pump.

5. The system of claim 1, wherein the user interface displays a graphical display area showing the plurality of infusion devices, the plurality of infusion channels, and the locations on the body of the patient.

6. The system of claim 5, wherein a click on a displayed infusion channel displays an infusion channel identifier that uniquely identifies the infusion channel.

7. The system of claim 5, wherein the location is a point on a vein of an arm of the body of the patient.

8. The system of claim 1, wherein the data associated with each infusion channel of the plurality of infusion channels displayed within the planning area comprises:

a patient identifier identifying the patient, a physical location of an infusion device connected to the infusion channel within a healthcare facility, an infusion device identifier identifying the infusion device, an anatomical location on a body of the patient where the medication is to be infused, a name of the medication to be infused, and a concentration of the medication to be infused.

9. The system of claim 1, wherein the user interface comprises a graphical user interface element associated with each infusion channel which, when activated, causes information about an alarm state for the corresponding infusion channel to be displayed.

* * * * *